(12) United States Patent
Maschke

(10) Patent No.: US 7,860,576 B2
(45) Date of Patent: *Dec. 28, 2010

(54) INTRAVENOUS PACEMAKER ELECTRODE

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 653 days.

This patent is subject to a terminal disclaimer.

(21) Appl. No.: 11/314,831

(22) Filed: Dec. 21, 2005

(65) Prior Publication Data

US 2006/0142660 A1     Jun. 29, 2006

(30) Foreign Application Priority Data

Dec. 23, 2004   (DE)   ................. 10 2004 062 395

(51) Int. Cl.
*A61N 1/05* (2006.01)
(52) U.S. Cl. ...................................... 607/116
(58) Field of Classification Search ............... 607/116, 607/119, 122, 123, 126
See application file for complete search history.

(56) References Cited

U.S. PATENT DOCUMENTS

| | | | |
|---|---|---|---|
| 5,193,546 A | | 3/1993 | Shaknovich |
| 5,273,546 A | * | 12/1993 | McLaughlin et al. ... 604/167.04 |
| 5,573,546 A | * | 11/1996 | Nakao .......................... 606/205 |
| 5,727,553 A | * | 3/1998 | Saad ........................... 600/407 |
| 5,968,085 A | * | 10/1999 | Morris et al. ............... 607/116 |
| 6,330,467 B1 | | 12/2001 | Creighton, IV et al. |
| 6,379,334 B1 | * | 4/2002 | Frassica .................. 604/165.04 |
| 2003/0097167 A1 | | 5/2003 | Friedman |
| 2003/0176786 A1 | * | 9/2003 | Maschke ..................... 600/435 |

FOREIGN PATENT DOCUMENTS

| | | |
|---|---|---|
| DE | 28 43 096 A1 | 4/1980 |
| DE | 33 00 050 A1 | 7/1984 |
| DE | 198 27 460 A1 | 12/1998 |
| DE | 102 03 371 A1 | 8/2003 |
| EP | 0 882 469 B1 | 12/1998 |

* cited by examiner

*Primary Examiner*—George R Evanisko
*Assistant Examiner*—Michael D'Abreu

(57) ABSTRACT

An intravenous pacemaker electrode has an electrode tip designed to release a drug, where the drug contains at least one of the active substances sirolimus, paclitaxel, everolimus, fibrin, rapamycin, and tacrolimus.

6 Claims, 4 Drawing Sheets

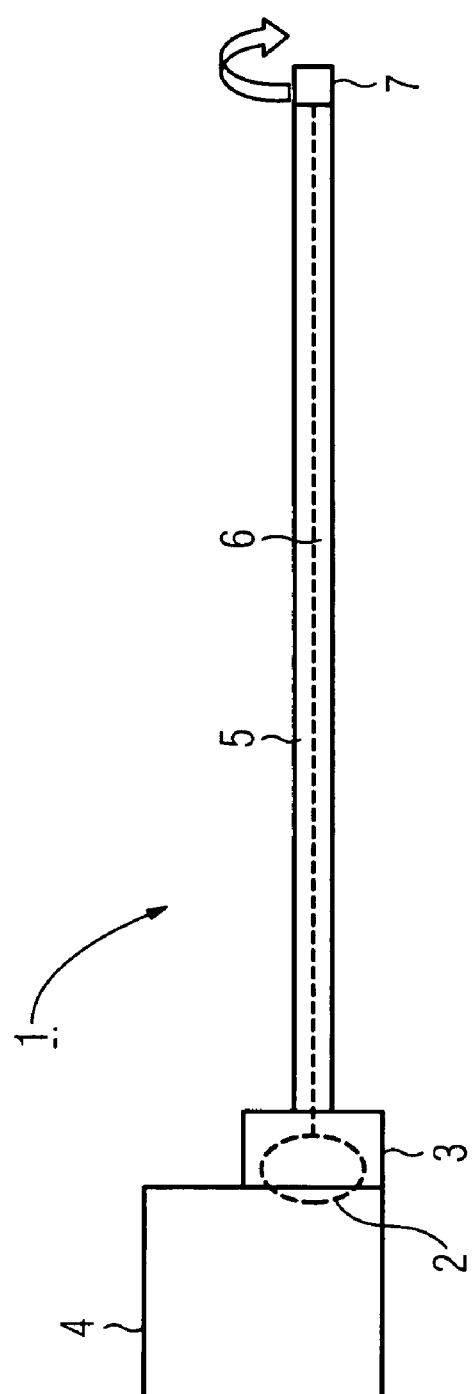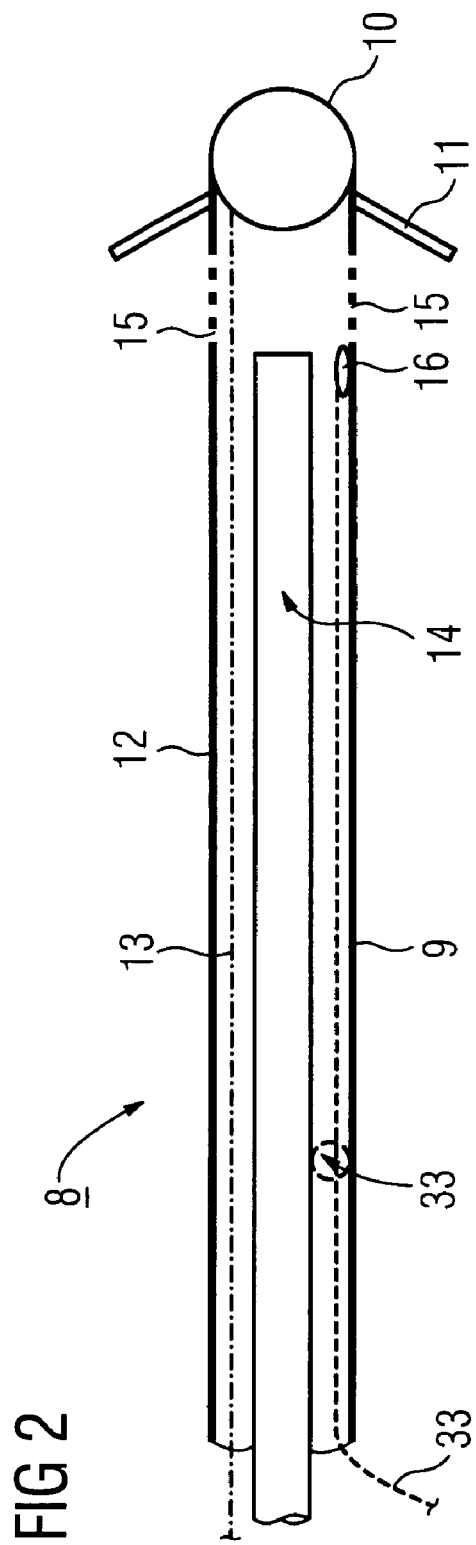

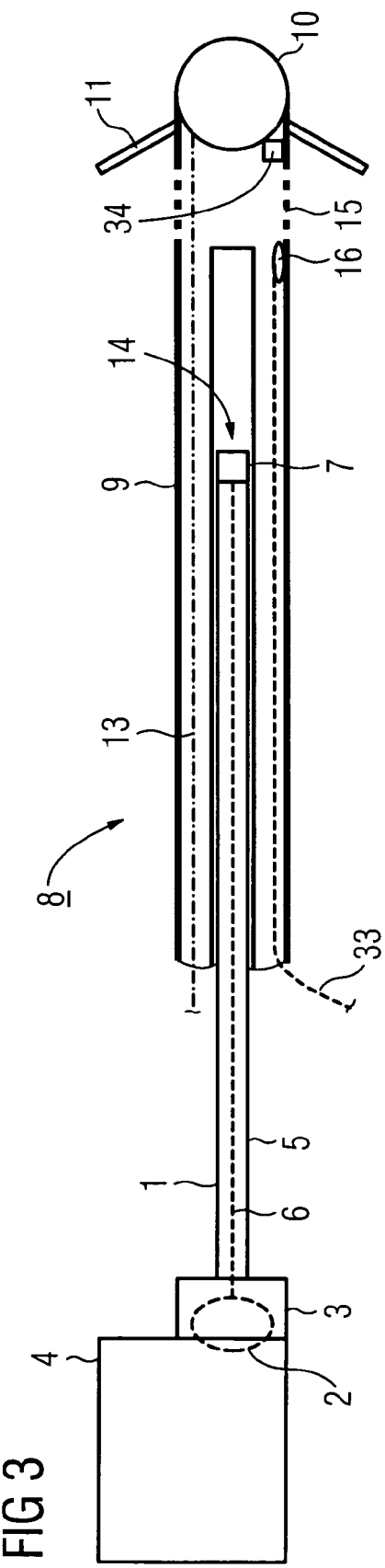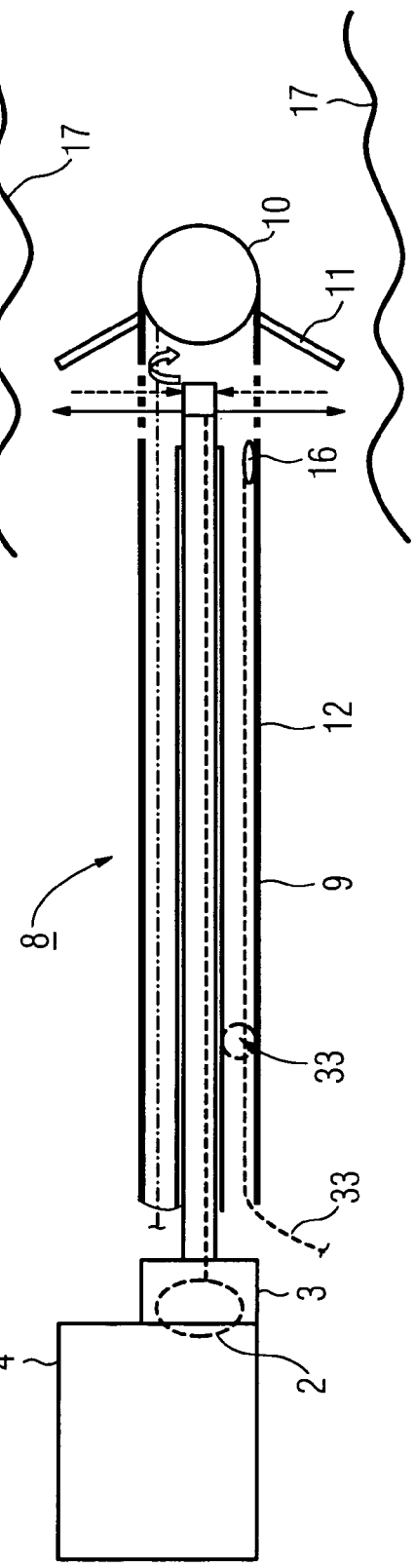

INTRAVENOUS PACEMAKER ELECTRODE

CROSS REFERENCE TO RELATED APPLICATION

This application claims priority of the German application No. 10 2004 062 395.3 DE filed Dec. 23, 2004, which is incorporated by reference herein in its entirety.

FIELD OF THE INVENTION

The invention relates to an intravenous pacemaker electrode with an electrode cable comprising a conductor, a duct and an insulating sleeve, with an electrode head being attached to the distal end of the line in order to transmit stimulation pulses.

BACKGROUND OF THE INVENTION

A pacemaker electrode of this type is known for example from DE 33 00 050 C2.

Pacemaker electrodes serve to transmit stimulation pulses from a pulse generator to the heart, in particular to the atrium and/or to the ventricle. The pacemaker electrodes can be advanced through a vein to the heart with the aid of an insertion instrument, this procedure typically being monitored using x-ray illumination. However, trabecular mesh of the ventricle is, in particular, a very thin soft tissue which is only visible, with difficulty, by means of an x-ray device. It is particularly difficult with known methods to establish whether the electrode tip of the pacemaker electrode is anchored to the tissue in the desired manner.

SUMMARY OF THE INVENTION

The object underlying the invention is to specify an intravenous pacemaker electrode which can be particularly effectively maneuvered during implantation.

This object is achieved according to the invention by an intravenous pacemaker electrode with the features of the claims as well as by a diagnosis and treatment device with the features of the claims.

The intravenous pacemaker electrode according to the invention comprises an electrode cable and an electrode head linked thereto, which is provided in order to transmit electrical stimulation pulses. A duct and a line leading to the electrode head run in an electrode cable comprising an insulating sleeve. An ultrasound catheter can be moved into the duct of the electrode cable, said ultrasound catheter comprising a thread-like guide element and an ultrasound measurement element attached to its distal end. The guide element of the ultrasound catheter preferably serves both to advance the ultrasound measurement element in the electrode cable as well as to transmit electrical signals. A measurement element is understood as an ultrasound measurement element, said measurement element comprising both an ultrasound emitter and also an ultrasound receiver. The combination of the pacemaker electrode with the ultrasound measurement element enables an imaging diagnosis with a good resolution in the heart. This diagnosis is particularly advantageous during x-ray illumination carried out simultaneously. The ultrasound catheter is not permanently linked to the remaining parts of the pacemaker electrode, but is however only inserted into the duct of the electrode cable if necessary.

The duct is preferably closed to such an extent that the ultrasound catheter cannot come into contact with the patient's blood or body tissue. Thus the ultrasound catheter can be used widely, even with different patients. The area of the electrode cable bordering the electrode head is preferably configured such that an ultrasound measurement is possible to a large extent uninfluenced by the material of the pacemaker electrode. For this purpose, an axial distance between the distal end of the duct and the electrode head is advantageous, with the ultrasound catheter, in particular its ultrasound measurement element, being able to be moved through the duct towards the electrode head. At least one window which is transparent for the ultrasound, for instance a window ring, is arranged in the area of the insulating sleeve of the electrode cable bordering the electrode head.

According to a preferred development, besides the duct for the ultrasound catheter, provision is made for a fluid duct suitable for conveying a contrast means towards the electrode head, and comprising an outlet opening in front of the electrode head. In contrast, provision can also be made for example to guide the contrast means through the same duct which is also suitable for inserting the ultrasound catheter. The use of a contrast means essentially broadens the diagnostic possibilities of the ultrasound examination. The outlet opening of the fluid duct preferably comprises a sealing device, which prevents body fluids from flowing into the electrode cable, in the manner of a non-return valve.

In addition to the duct for the ultrasound catheter and if necessary to the fluid duct for the contrast means, the electrode cable comprises an advantageous embodiment of a further guide duct provided for the insertion of a guidewire. The guidewire can also be identical to one of the aforementioned ducts. Independent of the total number of ducts in the electrode cable, provision is made according to a preferred development for an exit opening for the ultrasound catheter in the region of the electrode head. This allows the ultrasound measurement element to be moved past the electrode head, provided that the exit opening is located in the electrode head, even out via the electrode head.

Similar to the outlet opening for the contrast means, the exit opening for the ultrasound measurement element can also be preferably sealed by means of a valve. By way of example, this valve can be held in a closed state by means of spring force and opened by means of magnetic force. In this case, a magnet, in particular an electromagnet, is preferably arranged in the valve or mechanically coupled thereto.

A particularly reliable sealing of the exit opening for the ultrasound measurement element can be realized by means of a membrane, which closes the exit opening and is elastic such that the ultrasound catheter can be moved past the electrode head in the case of an exit opening remaining sealed. In this exemplary embodiment, the exit opening is preferably arranged at the distal end of the electrode head. In this exemplary embodiment, the ultrasound catheter is preferably rotatably arranged in a protective tube, which—without rotation—can be moved in the electrode cable and therebeyond.

To facilitate the navigation of the pacemaker electrode, the electrode head can be designed such that its movement state can be influenced by means of an external magnetic field. For this purpose, the electrode head preferably contains a magnet, in particular electromagnets, or is mechanically linked to such. An intravascular catheter with an element generating a magnetic field arranged in the catheter sleeve in the area of the catheter tip is known for instance from DE 102 03 371 A1. An electromagnet is preferably used here to generate the magnetic field on the catheter side, which can be emitted from outside of the patient and can be varied in terms of field intensity and field direction. A further magnetic system which can be used for medical purposes is known for example from U.S. Pat. No. 6,330,467 B1. This system can also be used with a flexible endoscope or catheter.

In a first embodiment the diagnosis and treatment device according to the invention comprises an intravenous pacemaker electrode as well as an evaluation unit interacting acting with its ultrasound measurement element, said evaluation unit being set up in a program-specific manner such that influences of the line of the electrode cable on the ultrasound measurement are at least computationally partially eliminated. The intravenous pacemaker electrode thus preferably comprises, however not necessarily, the features of the claims.

In a preferred embodiment, the evaluation unit allows the different pacemaker electrodes to be taken into consideration in computations. For this purpose, the evaluation unit is coupled to a data acquisition device which is provided to record data, in particular geometric data of the pacemaker electrode. Different line geometries can be practically shown from the ultrasound image.

According to a second embodiment the diagnosis and treatment device additionally comprises a telemetry module for intravenous pacemaker electrodes, in particular with the features of the claims, which is arranged in a pacemaker housing to which the electrode cable is connected and also comprises a data link to the ultrasound measurement element. The telemetry module allows the ultrasound measurement data to be read out even after the pacemaker has been implanted. The features of the two previously described exemplary embodiments of a diagnosis and treatment device are particularly advantageously combined. In this case the features of the first embodiment, in other words the computational consideration of the geometry of the pacemaker electrodes can be reduced within the implanted pacemaker or can be realized in an extracorporeal evaluation unit.

The invention is particularly advantageous in that an imaging diagnosis with good resolution is enabled in the heart by the combination of a pacemaker electrode with an ultrasound catheter which be arranged reversibly therein, whereby the risks involved with implantation are considerably reduced in comparison with an implantation exclusively undertaken using x-ray illumination.

BRIEF DESCRIPTION OF THE DRAWINGS

An exemplary embodiment of the invention is described below in further detail with reference to a drawing, in which;

FIG. 1 shows an ultrasound catheter for a pacemaker electrode

FIG. 2 shows a pacemaker electrode for use with an ultrasound catheter according to FIG. 1

FIG. 3,4 show a pacemaker electrode with partially and/or completely inserted ultrasound catheter.

DETAILED DESCRIPTION OF THE INVENTION

Figure 5:
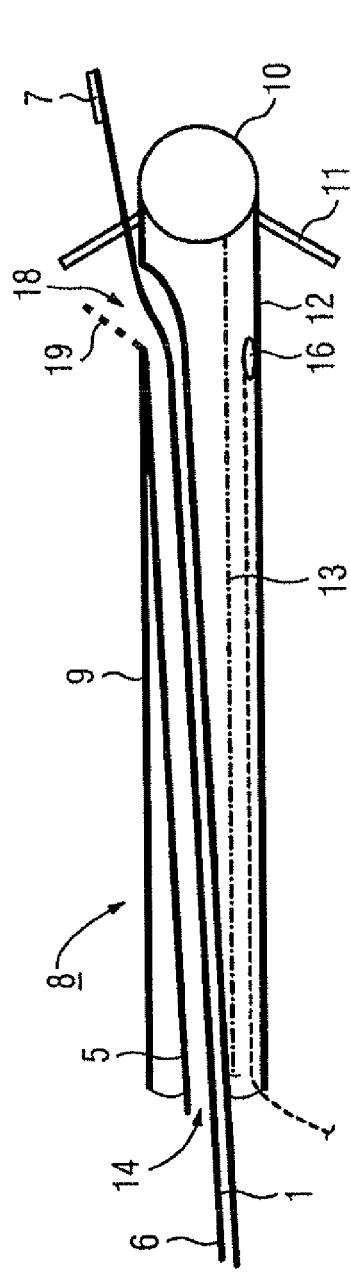
FIG. 5-7 show different embodiments of pacemaker electrodes with an ultrasound measurement element which can be moved past its electrode head and/or moved out via the electrode head.

Parts which correspond to each other or function identically are provided with the same reference characters in all the figures.

FIG. 1 shows an ultrasound catheter 1 for use in an intravenous pacemaker electrode (not shown here in further detail). The term pacemaker electrode is to be understood below in a broader sense and also comprises electrodes for ICD's (implantable cardioverters/defibrillators) for instance. An intravascular ultrasound system (IVUS) is known per se from DE 198 27 460 A1 as well as from U.S. Pat. No. 5,193,546 A. The ultrasound catheter 1 can also be used for stimulation electrodes for neurostimulation, which are inserted into the cranium in order to treat a patient with depression or Parkinson's disease for instance.

The ultrasound catheter 1 according to FIG. 1 is connected to a signal-interface/drive unit 4 for the IVUS examination with the aid of a mechanical linking system 3 comprising a rotation coupling 2. The ultrasound catheter 1 also referred to as an IVUS catheter comprises a covering 5 which serves as a drive shaft, also referred to as guide element, in which a signal line 6 runs which is linked to an ultrasound measurement element 7, also known as an IVUS sensor, at the distal end of the IVUS catheter 1. The IVUS sensor 7, as indicated by an arrow, can be rotated about its own axis during the examination with the aid of the signal-interface/drive unit 4.

FIG. 2 shows an intravenous pacemaker electrode 8 suitable for use with an ultrasound catheter 1 according to FIG. 1.

This is a combination of an electrode cable 9 and an electrode head 10 attached its distal end. The electrode head 10, also known as the electrode tip, serves as a cathode of the pacemaker and is provided for contacting the atrium or the ventricle of the heart. In the embodiment displayed, the pacemaker electrode 8 is suitable for instance for a pacemaker which operates with only one electrode as a so-called one-chamber system. Likewise the pacemaker 8 shown can also be used in pacemakers operating with two electrodes, with an electrode being guided to the atrium and to the ventricle in each instance. The pacemaker operating with the pacemaker electrode 8 and not shown in further detail in FIG. 2 can comprise features for instance of an implantable heart support device known from EP 0 882 469 469 B1, and can also identify and classify the cardial activity in order to transmit stimulation pulses. The pacemaker known from EP 0 882 469 B1 is a device operating using unipolar pacemaker electrodes. In this case, the pacemaker electrode functions as a cathode and the housing of pacemaker as an anode. Likewise the pacemaker electrode 8 displayed section by section can also be used as a part of a pacemaker operating with bipolar pacemaker electrodes, with a special anode being arranged in the distal electrode region in this case.

The electrode head 10 comprises a number of fixing aids 11 in the form of fold-out anchor appendages, which engage in the trabecular tissue of the heart chambers in the manner of an anchor and ensure both the mechanical fixing as well as a low-resistance transmission of the stimulation pulses to the myocardium. A possible embodiment of the electrode fixing aids in the form of a wire spring arrangement is known in detail for instance from DE 28 43 096 A1. Notwithstanding the simplified form displayed according to FIG. 2, the fixing aids 11 can also comprises a form known from DE 33 00 050 C2 for instance, which both protects this during the insertion of the electrode through a vein and also prevents body fluid from infiltrating into the electrode. The electrode head 10 including the fixing aids 11 has a surface made of iridium for instance, which exhibits particularly good electrical contacting attributes and thus allows an especially artifact-free perception of signals.

The covering of the electrode cable 9 is formed by an insulating sleeve 12, within which runs a line 13 inter alia connected to the electrode head 10. Furthermore, a duct 14 is located in the electrode cable 9, which is suitable for inserting the ultrasound catheter 1 (FIG. 1). The distal right end of the duct (in the diagram) is somewhat remote from the electrode head 10, so that the ultrasound catheter 1 can be moved approximately through the duct 14 towards to the electrode head 10. In this area, the insulating sleeve 12 comprises essentially transparent windows 15 or a window ring for ultrasound. The line guide of the electrode cable 9 is accordingly adjusted in the region of the window 15 or the window 15. Furthermore, it is possible, as described in greater detail below, to minimize influences of the line guide on the intravascular ultrasound measurement in a control or software-specific manner.

The pacemaker 8 is also suitable for conveying contrast means for the ultrasound examination and for this purpose comprises an outlet opening 16 in the insulating sleeve 12 near to the electrode head 10, next to the windows 15. The contrast means flowing through the electrode cable 9 to the outlet opening 16 is indicated by the dashed line. The outlet opening 16 is designed as a miniaturized non-return valve, thereby intentionally allowing the contrast means to flow out directly into the heart chamber, but nevertheless preventing the blood from infiltrating into the lumen of the electrode cable 9. Thus the ultrasound catheter 1 very rarely comes into contact with the body fluid of the patient, and only does so when the ultrasound examination is supplied with a contrast means, which has hitherto been practiced together with external ultrasound applicators and can thus be readily widely used. The non-return valve 16 is preferably manufactured using nanotechnology methods, in other words in particular with methods used in the field of semiconductor technology including etching technology and lithography. The same applies to other miniaturized parts of the intravenous pacemaker electrode 8.

The lumen, through which the contrast means is fed, can be identical to the duct 14 for the ultrasound catheter 1 or to another hollow chamber, or, as in the exemplary embodiment according to FIG. 2, can be designed as a special fluid duct 33. The same applies to the potential combination of the duct 14 with a duct for a guidewire of the pacemaker electrode 8. In each case, contrast means can be fed through the duct 14 in order to improve the x-ray and/or ultrasound display. Sealing plugs are provided at the end of the pacemaker electrode 8 which is not shown, to which the actual pacemaker is to be connected. The pacemaker electrode 8 preferably comprises a separate duct 14 which is solely provided for inserting the ultrasound catheter 1 and is preferably located in the middle of the electrode cable 9, as shown in FIG. 2. The centrical arrangement of the duct 14 is particularly advantageous in that the ultrasound measurement element 7 is thus centered in the electrode cable 9. Silicon or polyurethane can be used as the wall material of the duct 14 for instance, as well as for other insulating parts of the electrode cable 9.

FIGS. 3 and 4 show the introduction of the ultrasound catheter 1 into the electrode cable 9 of the pacemaker electrode 8. Tissue walls 17 are indicated in FIG. 4 which are to be examined by ultrasound. The ultrasound measurement element 7 which is arranged at the distal end of the ultrasound catheter 1 transmits and receives ultrasound signals, with transmitted signals being indicated in FIG. 4 by continuous arrows and reflected signals by dashed arrows. The ultrasound measurement element 7 is arranged pivotably with the complete ultrasound catheter 1 in the duct 14 of the electrode cable 9. Unlike the depiction in the diagram, when the electrode cable 9 is moved, the fixing aids 11 are folded towards the electrode head 10, in contrast to the display. It is particularly advantageous that in order to rotate the ultrasound measurement element 7 about the longitudinal axis of the electrode cable 9, this does not need to be completely rotated, in other words a rotation of the thread-like guide element 5 within the electrode cable 9 is sufficient.

The ultrasound catheter 1 is different from FIGS. 3 and 4, and can also be combined with a special catheter for diagnostic or treatment purposes. This is just as advantageous during use as part of the pacemaker electrode 8, such that the ultrasound catheter 1 does not come into contact with patients' tissue or body fluid. As shown in FIG. 3, the electrode head 10 has a magnet 34, preferably an electromagnet which can be controlled by means of the electrode cable 9, which allows the pacemaker electrode 8 to be magnetically navigated in the body of the patient in conjunction with an external magnetic field.

Figure 6:
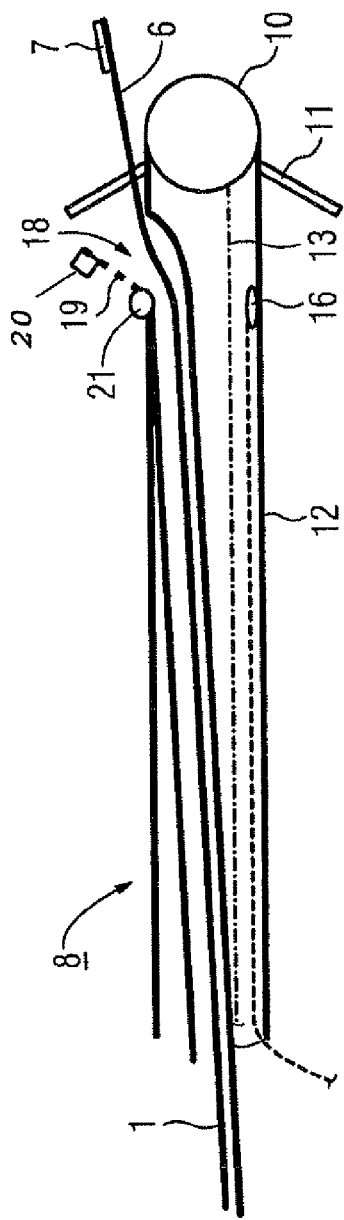
Figure 7:
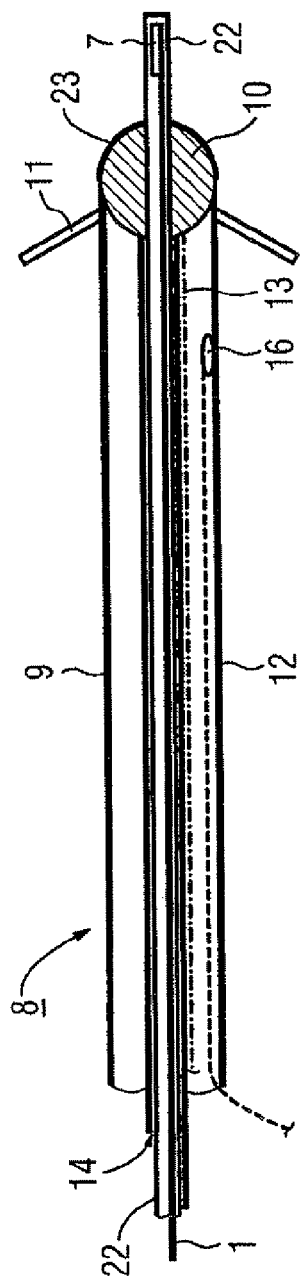

FIGS. 5 to 7 show developments of the pacemaker electrode 8, which allows wider use of the ultrasound catheter 8. In the exemplary embodiment according to FIGS. 5 and 6, the insulating sleeve 12 features a valve 19 near to the electrode head 10, approximately at the height of the outlet opening, said valve sealing an exit opening 18 of the duct 14 in a closed state. The ultrasound measurement element 7 can be moved out of the electrode cable 9 and moved past the electrode head by means of this valve, which is designed approximately according to the principle of a heart beat or in the manner of a drainage hole. The valve is opened for instance by force effect of the ultrasound measurement element 7 when the ultrasound catheter (FIG. 5) is pushed forward. In the embodiment according to FIG. 6, the valve 19 comprises a magnet 20 and a support with a spring element 21, which retains the valve 19 in a closed state without further force effect. The magnet 20, preferably a permanent magnet, serves to open the valve 19 with the aid of an intense external magnetic field if necessary. Independent of the detailed mode of operation of the valve 19, this is preferably designed as a non return valve, so that no blood can infiltrate into the duct 14 of the electrode cable 9. An exposure of the ultrasound measurement element 7 to body fluid is nevertheless not to be avoided in the embodiments according to FIGS. 5 and 6.

In contrast to this, the ultrasound catheter 1 in the embodiment according to FIG. 7 remains completely shielded from the body fluid of the patient. For this purpose, the actual catheter is located in a protective tube 22, in which it can be rotated. The protective tube 22 which is not rotated can be moved directly over the distal end of the electrode head 10. In this connection, the protective tube 22 penetrates an elastic membrane 23, made of silicon for instance, which automatically reseals itself after the protective tube 22 has been removed.

Figure 8:
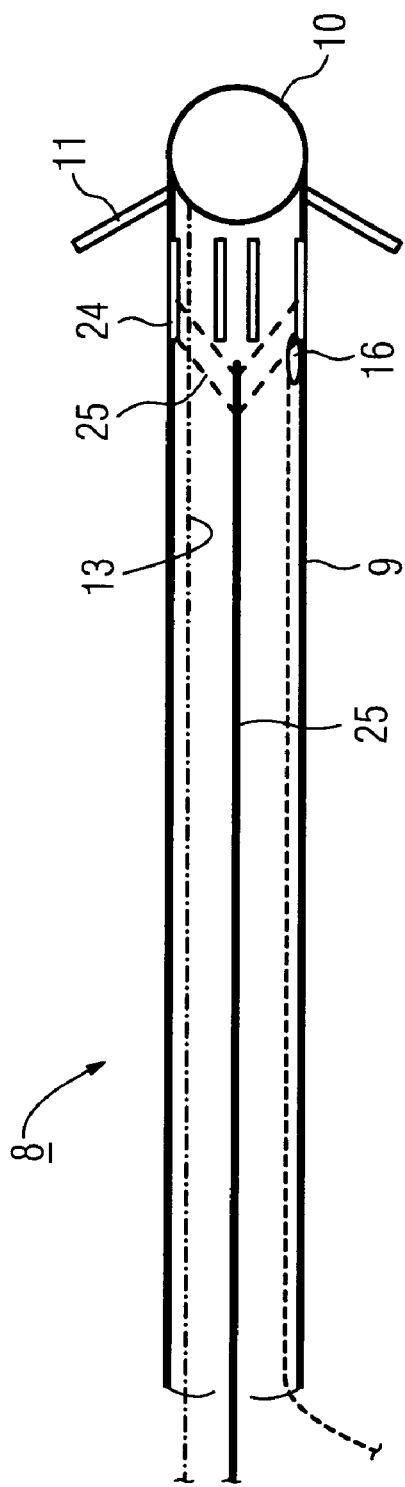
FIG. 8 shows a pacemaker electrode with annular ultrasound sensor array.

An alternative embodiment of a pacemaker electrode 8 which does not require a rotatable support of an ultrasound catheter is shown in FIG. 8. In this connection an annular ultrasound sensor array 24 is located in the area of the electrode cable 9 bordering the electrode head 10. Multiple control and signal lines 25 lead to the sensor array 23. The number of control and signal lines 25 fed through the electrode cable 9 can be reduced (not shown in further detail) by using a multiplexer arranged on the sensor array 24. In addition, the line 13 connected to the electrode head 10 can also be used at least temporarily for the ultrasound measurement.

Figure 9:
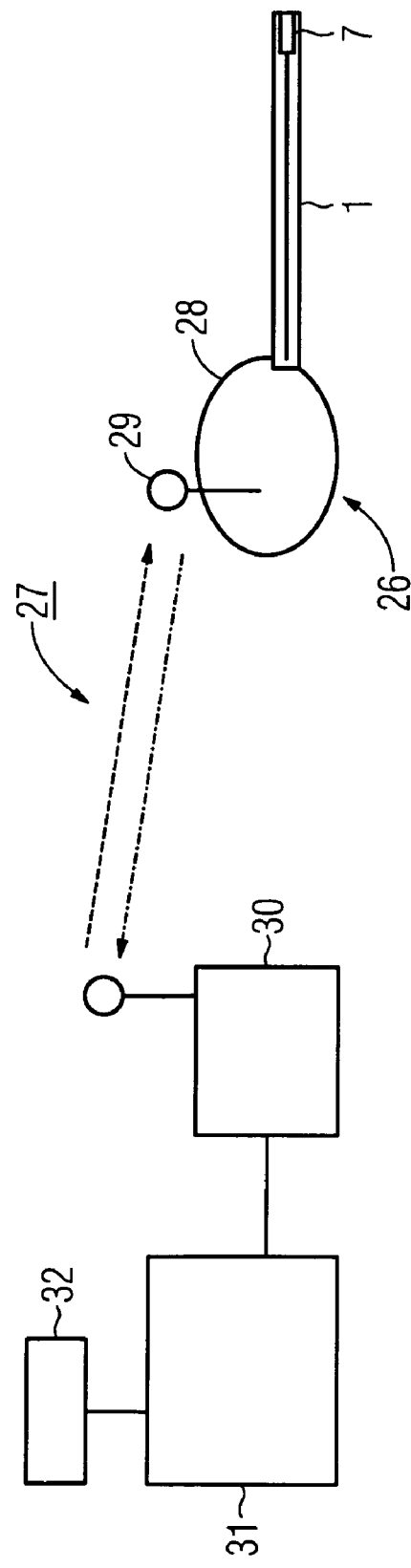
FIG. 9 shows a pacemaker with an ultrasound measurement element integrated into the telemetry system.

FIG. 9 shows the inclusion of a pacemaker 26 with integrated ultrasound catheter 1 in a telemetry system 27. For this purpose, the pacemaker 26 linked to the pacemaker electrode 8 comprises a first, transceiver unit 29, arranged in the pacemaker 28 or connected thereto for the wireless transmission of signals in particular radio signals. A pre-processing and control unit (not shown in further detail) is located within the pacemaker housing 28, said pre-processing and control unit being provided for a first processing of the data recorded by means of the ultrasound measurement element 9.

A second transceiver unit 30, also known as telemetry interface, communicates with the first transceiver unit 29, also referred to as telemetry module, which is thus found in the body of the patient, outside of the body of the patient. The telemetry interface 30 is in turn connected to an evaluation unit 31 in a conducted or wireless manner.

In this way, an ultrasound examination which can be externally influenced and evaluated cannot only be carried out whilst the pacemaker electrode 8 is being implanted, but also at any later point with the aid of the telemetry module 29 linked to the ultrasound measurement element 7 in a data-specific manner. A long-term monitoring of a patient is particularly possible by means of repeated ultrasound examinations using the implanted ultrasound catheter 1. It is particularly advantageous to integrate a pacemaker electrode 8 according to FIG. 8 in the telemetry system 27 according to FIG. 9, since in this case the mechanical rotation of parts within the pacemaker electrode 8 is not necessary.

The functions of the evaluation unit 31 can also be realized in whole or in part within the pacemaker 28. Such a function, for instance the computational consideration of the geometry of the electrode cable 9, in particular of the line 13, during the ultrasound examination. For this purpose, a data acquisition device 32, in the form of a scanner for instance, is connected to the evaluation unit 31. The geometric data and other relevant data of the potentially used pacemaker electrode 8 is stored in a database, and can be assigned to a barcode which is applied to the packaging of the pacemaker electrode 8 and is read with the aid of the data acquisition device 32. The evaluation unit 31 uses this data to generate an at least essentially artifact-free ultrasound image which particular eliminating influences of the line 8 from the signals obtained by means of the ultrasound measurement element 7.

The invention claimed is:

1. An intravenous pacemaker electrode with an electrode cable, comprising:
    a line;
    a catheter duct;
    an insulating sleeve covering the catheter duct and the line;
    an electrode head attached to a distal end of the line adapted to transmit stimulation pulses;
    an ultrasound catheter that is moved in the catheter duct and comprising a thread-like guide element and an ultrasound measurement element attached to a distal end of the ultrasound catheter;
    a special fluid duct;
    a fluid duct outlet opening of the special fluid duct arranged in the insulation sleeve proximal to the electrode head, the special fluid duct being adapted to convey a contrast means towards the electrode head;
    a sealing device provided at the fluid duct outlet opening and configured as a non-return valve, wherein the sealing device allows contrast means to flow through the special fluid duct and out from the fluid duct outlet opening but prevents a reverse flow into the electrode cable via the fluid duct outlet opening;
    wherein a sealing valve is arranged in a region of the electrode head that is axially distanced from the electrode head;
    wherein the path of the catheter duct extends directly to the sealing valve;
    and wherein when the appropriate pushing force is applied to the ultrasound measurement element, the appropriate pushing force opens the sealing valve and the ultrasound measurement element is moved through the sealing valve and past the electrode head.

2. The pacemaker electrode according to claim 1, wherein the distal end of the catheter duct is axially distanced from the electrode head such that the ultrasound catheter can be moved along the catheter duct towards the electrode head.

3. The pacemaker electrode according to claim 1, wherein the catheter duct for the ultrasound catheter is separated from a guide duct provided for the insertion of a guide-wire.

4. The pacemaker electrode according to claim 1, wherein an exit opening is arranged in the region of the electrode head.

5. The pacemaker electrode according to claim 1, further comprising a magnet mechanically linked to the electrode head for influencing the movement of the electrode head by an external magnetic field.

6. The pacemaker electrode according to claim 5, wherein an electromagnet is provided as the magnet.

* * * * *